United States Patent [19]

Mader et al.

[11] Patent Number: 5,512,185

[45] Date of Patent: *Apr. 30, 1996

[54] PURIFICATION OF STABLE ORGANIC COMPOUNDS

[75] Inventors: Roger A. Mader, Stillwater; Robert J. Ryther, St. Paul, both of Minn.

[73] Assignee: Minnesota Mining and Manufacturing Company, St. Paul, Minn.

[*] Notice: The portion of the term of this patent shall not extend beyond the expiration date of Pat. No. 5,443,747.

[21] Appl. No.: 508,383

[22] Filed: Jul. 31, 1995

Related U.S. Application Data

[62] Division of Ser. No. 335,450, Nov. 7, 1994, Pat. No. 5,443,742.

[51] Int. Cl.$^6$ .................................................. C02F 1/72
[52] U.S. Cl. ........................ 210/758; 544/237; 430/617; 430/965
[58] Field of Search ........................... 210/758; 430/617, 430/965; 544/237

[56] References Cited

U.S. PATENT DOCUMENTS

| | | | |
|---|---|---|---|
| 4,011,219 | 3/1977 | Nishii et al. | 544/237 |
| 4,123,282 | 10/1978 | Winslow. | |
| 4,585,734 | 4/1986 | Weigel | 430/619 |

OTHER PUBLICATIONS

"Reagents for Organic Synthesis," by Louis F. Fieser and Mary Fieser, p. 1011.

*Primary Examiner*—Neil McCarthy
*Attorney, Agent, or Firm*—Gary L. Griswold; Walter N. Kirn; Mark A. Litman

[57] ABSTRACT

Metal oxidizing agents (such as silver oxide or silver nitrate) are added to a solution of organic chemicals which comprise an unwanted level of organic reducing agents (either aqueous or organic solutions in which the metal oxidizing agent does not dissolve) and the metal oxidizing agent oxidizes at least some portion of said organic reducing agents. Because the metal oxidizing agent is insoluble in the solution, it is readily removed (e.g., by filtration or sedimentary techniques) to leave a solution with reduced amounts of reducing agents therein. This process is particularly useful for purifying phthalazine, behenic acid, and other toners, the component forming the counterion with silver ion in forming the light-insensitive silver source material and any other additives and raw materials which can be dissolved in a solvent medium in which the metal oxidizing agent is not highly soluble.

16 Claims, No Drawings

PURIFICATION OF STABLE ORGANIC COMPOUNDS

This is a division of application Ser. No. 08/335,450 filed Nov. 7, 1994, now U.S. Pat. No. 5,443,742.

BACKGROUND OF THE INVENTION

1. Field of the Invention

The present invention relates to the preparation or purification of organic chemicals, and particularly to compounds which are to be added to photothermographic compositions and elements.

2. Background of the Art

Standard purification methods for chemical compounds, including those used in photothermographic elements comprise such conventional treatments as solvent extraction, recrystallization, chromotography, vacuum distillation, and other well known physical and chemical treatments. These procedures are useful with the purification of many different compounds, but have been found to be particularly ineffective in the purification of certain active agents for use in photothermography, where the presence of strong silver reducing agents is particularly damaging to the composition.

Silver oxide or silver nitrate on silica gel or alumina are well known in standard chemical procedures as agents which oxidized (by chemical reaction) to remove certain organic compounds. These are also used as reagents in organic synthetic procedures.

BRIEF DESCRIPTION OF THE INVENTION

Metal oxides or metal nitrates (as particulates or supported), such as silver oxide or silver nitrate, are added to a solution of organic chemicals which comprise an unwanted level of organic reducing agents (either aqueous or organic solutions in which silver oxide does not dissolve) and the silver oxide oxidizes at least some portion of said organic reducing agents. Because the silver oxide is insoluble in the solution, it is readily removed (e.g., by filtration or sedimentary techniques) to leave a solution with reduced amounts of reducing agents therein. This process is particularly useful for purifying phthalazine, behenic acid, and other toners, the component forming the counterion with silver ion in forming the light-insensitive silver source material and any other additives and raw materials (which can be dissolved in a solvent medium in which the silver oxide is not highly soluble, less than 5% by weight silver oxide is soluble in the solvent medium, preferably less than 3%, more preferably less than 1% by weight of said solvent) to the photothermographic composition (except for the reducing agent for silver ion).

DETAILED DESCRIPTION OF THE INVENTION

A process for improving the performance and/or purity of additives or raw materials, particularly those used in photothermographic elements, comprising providing a solution of an organic compound having silver ion reducing agent impurities therein, adding an inorganic oxidizing agent, such as a metal oxide or metal nitrate oxidizing agent, such as silver oxide, to the solution without said metal oxide or metal nitrate forming a solution of 5% or more by weight silver oxide to the solvent of said solution, oxidizing said reducing agent impurity with said silver oxide, and removing undissolved silver oxide from said solution.

Individual raw materials used in photothermographic coatings are dissolved or slurried in a suitable solvent, added to this solution or slurry is an inorganic oxidizing agent that is not soluble in the solution (i.e., it is heterogeneous to the raw material) either because the inorganic oxidizing agent itself is not soluble in the solution or the inorganic oxidizing agent is bonded to an insoluble support (as with a flake, a particle or platelet on which the inorganic oxidizing agent is bonded). The solution containing the raw material and the inorganic oxidizing agent is then mixed and heated (to accelerate the oxidation process) until sufficient or complete oxidation of silver ion reducing contaminants in the raw material has occurred. This can be determined analytically or by sampling. Sampling may be done by taking a portion for use in a photothermographic coating compared to a control coating. At this point, other cleaning procedures could be attempted on the solution such as the use of carbon black for removal of colored compounds that do not cause silver reduction in photothermographic coatings but may be undesirable because of the color added to the coatings.

The solution may then be filtered to remove the inorganic oxidizing agent, the material reduced by the silver reducing compounds and material from other purification procedures. The oxidized species often appears to be removed along with the silver oxide residue, either within pores in the silver oxide, as a complex with the silver oxide, as a salt or reaction product with the silver oxide, absorbed on an ingredient, or in some other manner. The resulting processed raw material can then be dried or recrystallized as desired with a near 100% yield. The inorganic oxidizing agent or the solid support can act to hold onto the material reduced by the silver reducing compounds thereby removing from the raw material all reducing species in the process of filtering.

There have been no significant adverse residues of the organic oxidizing agent for silver ion in the treated solutions after removal of the silver oxide.

Suitable inorganic oxidizing agents include such materials as metal oxides and nitrates, such as silver oxide (AGO), silver nitrate, manganese dioxide ($MnO_2$), lead oxide (PbO), lead nitrate, and other metal oxides which can be used as non-soluble components in the removal of silver reducing agents, particularly from photothermographic raw materials. These and other oxidizing agents can be classified for their oxidizing capabilities by their oxidizing potentials, their surface activity and their insolubility in the desired processing solvent. Both surface activity and solubility of these and other oxidizing agents can be altered to benefit the processing by chemically or physically binding the inorganic oxidizing agents to inert solid supports such as polymers, alumina, silica, zeolites or other inert solid supports to keep the oxidizing agents and/or their subsequent reduced forms in an insoluble state to permit removal from the raw material to be cleaned by filtration.

The process of this invention can be used with any organic compounds in which it is undesirable to have oxidizing species, particularly any of the raw materials used in photothermographic compositions which are susceptible to impurities. These impurities may appear in quantities that vary lot to lot and cause silver reduction in the photographic coatings and thereby negatively alter sensitometric properties. The application of the processing by the heterogeneous inorganic oxidation method can, therefore, be broadly applied to raw materials used in photothermographic coatings such as toners (e.g., phthalazine, phthalazinone, etc.), anionic counterion forming materials for the silver ion in the light-insensitive silver source material (e.g., behenic acid, benzimidazole, complexing agents, organic acids in general and long chain carboxylic acids in particular, etc.), and any other class of additive, except for the reducing agents for silver ion which are essential to the photothermographic process.

The solvent system in the heterogeneous inorganic oxidation method is only important with respect to dissolving or adequately slurrying the organic compound or raw material of interest in order that the raw material may be completely separated from the essentially insoluble inorganic oxidizing compound or the inorganic oxidizing agent bound to a solid support. Possible solvent systems include acetone, 2-butanone and other ketone solvents, hydrocarbons such as toluene and hexane, alcohols such as methanol as well as water and aqueous based solvent systems.

EXAMPLE

Phthalazine Processing by AgO in Acetone with Refluxing

Phthalazine is a desirable photothermographic toner system and has had inconsistent results in photothermography over a period of decades due to a number of silver reducing agents formed in the phthalazine process. Multiple processes have been used in the synthesis of phthalazine with purity levels consistently near 99% and yet the presence of the very strong silver reducing agents remaining in the phthalazine have often resulted in unacceptably high minimum photographic densities in Dry Silver systems. Other methods of purification of phthalazine have been attempted including solvent extraction of the silver reducing impurities and vacuum distillation. Solvent extractions are effective only with multiple extractions and recrystallizations using chlorinated solvents, such treatment has a low yield of photographic grade phthalazine and is environmentally unacceptable. Vacuum distillations of phthalazine have been effective in purifying phthalazine on a laboratory scale but on a larger scale explosions have resulted in the distillation in multiple configurations.

The use of a heterogenous oxidizing system to eliminate the silver reducing species in phthalazine is ideal in that it uses only inexpensive, environmentally acceptable and recoverable solvents and oxidizing agents, results in a nearly 100% yield of photographic grade phthalazine, is much more cost efficient overall than the solvent extraction/recrystallization method or the vacuum distillation method and can be added as a final step in the phthalazine synthesis process with little difficulty or added expense. In addition, as there are a number of colored compounds in the phthalazine that do not reduce silver but add undesired color to the photographic system, the heterogenous oxidizing system is amenable to the use of carbon black to eliminate some or all of the colored compounds in the same processing step as the inorganic oxidizing agent as both the inorganic oxidizing agent and the carbon black can be filtered out simultaneously without jeopardizing the processing, the cost or the recovery of the inorganic oxidizing agent for recycling.

Analytical results using high performance liquid chromatography (HPLC) and thin layer chromotography (TLC) demonstrate that phthalazine processed using the heterogenous oxidizing system eliminated chromatographic peaks associated only with the impurities that were found to be silver reducing agents in Dry Silver.

A production lot of phthalazine that had been initially rejected for photographic use due to high minimum photographic density was processed by the heterogenous oxidizing method and was used in a typical Dry Silver photographic application.

A mixture containing 300 grams of phthalazine (contaminated with silver reducing agents), 6.0 grams of silver (I) oxide and 1154 grams of acetone was stirred and heated at reflux for 8 hours. After this time the mixture was cooled to 25° C. Ten grams of activated carbon were added and the mixture stirred for 15 minutes. The reaction mixture was then filtered through a filter agent. Some of the acetone solvent (527 grams) was removed by distillation, and 400 grams of heptane was added. The distillation was continued until the pot temperature reached 70° C. The mixture was cooled with agitation to 25° C. and the solid filtered. This solid was dried to give 275 grams of photographic grade phthalazine.

In that photothermographic application, the processed phthalazine behaved better than a control for minimum photographic density without affecting other sensitometric properties. The control phthalazine had not been processed using the heterogenous oxidizing method and was considered to give a very good minimum photographic density for that Dry Silver application.

A high purity commercially available "reactive" phthalazine compared to the same phthalazine after the reprocessing with AgO (as described above) gave the following minimum photographic densities in two standard silver halide based photothermographic coatings:

|  | Dmin (15 sec at 250° F.) | Dmin (30 sec at 250° F.) |
| --- | --- | --- |
| Reactive Phthalazine | 0.275 | 0.455 |
| (repeat) | 0.263 | 0.446 |
| Purified Phthalazine | 0.256 | 0.410 |
| (repeat | 0.258 | 0.399 |

The effect of the reprocessed phthalazine was more pronounced under more reactive (higher temperature) conditions for Dry Silver. No photothermographic sensitometric properties were adversely altered in this process.

A second source of commercially available 99% purity phthalazine was used in a duplicate experiment. Although both commercial phthalazines were indicated as 99% pure, the variation in the amount of reactive impurities can vary significantly as shown by the following data, similar to that presented above.

|  | Dmin (15 sec at 250° F.) |
| --- | --- |
| Reactive Phthalazine | 2.770 |
| Purified Phthalazine | 0.247 |

The dramatic ability of the practice of the present invention to improve the photothermographic quality of phthalazine toners is clearly shown by this data.

What is claimed is:

1. A process for removing undesirable reducing compounds from an organic material used as a raw material in photothermographic compositions comprising the steps of:

a) providing said organic material with undesirable reducing compounds in a liquid carrying medium, b) adding to said liquid carrying medium and organic material at least one metal oxidizing agent, said oxidizing agent being added in a quantity sufficient to substantially prevent undesired silver reduction caused by said reducing compounds in photothermographic coatings, c) oxidizing said undesirable reducing compounds, and d) removing said metal oxidizing agent from said liquid carrying medium.

2. A process for removing undesirable reducing compounds from a liquid organic material used as a raw material in photothermographic compositions comprising the steps of:

a) providing said organic material with undesirable reducing compounds in a liquid carrying medium, b) adding to said liquid carrying medium and organic material at least one metal oxidizing agent, said oxidizing agent being added in a quantity sufficient to substantially prevent undesired silver reduction caused by said reducing compounds in photothermographic coatings, c) oxidizing said undesirable reducing compounds, and d) removing said metal oxidizing agent from said liquid organic material.

3. The process of claim 1 wherein said metal oxidizing agent comprises a metal oxide or metal nitrate.

4. The process of claim 2 wherein said metal oxidizing agent comprises a metal oxide or metal nitrate.

5. The process of claim 3 wherein d) forms a purified organic material which is then added to a photothermographic layer coating composition.

6. The process of claim 4 wherein d) forms a purified organic material which is then added to a photothermographic layer coating composition.

7. The process of claim 5 wherein said organic material is a toning agent for silver halide based photothermographic imaging.

8. The process of claim 6 wherein said organic material is a toning agent for silver halide based photothermographic imaging.

9. The process of claim 3 wherein said oxidizing agent comprises silver oxide.

10. The process of claim 4 wherein said oxidizing agent comprises silver oxide.

11. The process of claim 5 wherein said oxidizing agent comprises silver oxide.

12. The process of claim 6 wherein said oxidizing agent comprises silver oxide.

13. The process of claim 7 wherein said oxidizing agent comprises silver oxide.

14. The process of claim 8 wherein said oxidizing agent comprises silver oxide.

15. The process of claim 1 wherein said oxidizing agent comprises silver nitrate on a particulate support.

16. The process of claim 15 wherein said oxidizing agent comprises silver nitrate on silica gel or on alumina.

* * * * *